US006543444B1

(12) United States Patent
Lewis

(10) Patent No.: US 6,543,444 B1
(45) Date of Patent: Apr. 8, 2003

(54) SYSTEM AND METHOD FOR AIR TIME REMAINING CALCULATIONS IN A SELF-CONTAINED BREATHING APPARATUS

(76) Inventor: John E. Lewis, 4524 Palos Verdes Dr. East, Rancho Palos Verdes, CA (US) 90275

( * ) Notice: Subject to any disclaimer, the term of this patent is extended or adjusted under 35 U.S.C. 154(b) by 0 days.

(21) Appl. No.: 09/546,292

(22) Filed: Apr. 10, 2000

(51) Int. Cl.$^7$ .............................................. A61M 15/00

(52) U.S. Cl. ............................ 128/200.24; 128/205.23; 128/201.27; 128/898

(58) Field of Search ............................ 128/898, 200.24, 128/201.27, 204.18, 205.11, 204.26, 205.15, 205.22, 205.24, 205.23

(56) References Cited

U.S. PATENT DOCUMENTS

| | | | | |
|---|---|---|---|---|
| 3,681,585 A | | 8/1972 | Todd | |
| 3,992,948 A | | 11/1976 | D'Antonio et al. | |
| 4,005,282 A | | 1/1977 | Jennings | |
| 4,054,783 A | | 10/1977 | Seireg et al. | |
| 4,586,136 A | | 4/1986 | Lewis | |
| 4,882,678 A | | 11/1989 | Hollis et al. | |
| 4,970,897 A | | 11/1990 | Budinger | |
| 5,016,483 A | | 5/1991 | Budinger | |
| 5,570,688 A | * | 11/1996 | Cochran et al. | 128/205.23 |
| 5,617,848 A | * | 4/1997 | Cochran | 128/205.23 |
| 5,794,616 A | * | 8/1998 | Cochran et al. | 128/205.11 |
| 5,899,204 A | * | 5/1999 | Cochran | 128/205.23 |

FOREIGN PATENT DOCUMENTS

| | | |
|---|---|---|
| EP | 0 919 462 | 2/1999 |

OTHER PUBLICATIONS

Busuttili et al., "Sport Diving: The British Sub–Aqua Club Diving Manual," 1988, pp. 100–103 and 115–117, XP–002168940, Stanley Paul & Co. Ltd., London.

* cited by examiner

*Primary Examiner*—Glenn K. Dawson

(57) ABSTRACT

A method and apparatus for accurately determining air time remaining in a self-contained breathing apparatus quantifies the effects of various non-linearities in order to define an accurate estimate of air time remaining within a gas supply tank. An analytical expression relates a mass equivalent to measured tank pressure through a power function. The system determines the rate of change of pressure with respect to time in order to determine numerical values for a rate of change of mass equivalent with respect to time, as well as the values of a set of constants relating mass equivalent to the pressure power function. A range of pressure:mass equivalent data pairs are produced which express the pressure/mass equivalent relationship over a range of specified mass equivalents. A function is curve fit to the data points in order to develop an expression which relates mass as a function of pressure directly or various pressure:mass equivalent data points are stored in a look-up table and, for any given measured pressure, a corresponding mass can be determined by simply consulting the table.

11 Claims, 4 Drawing Sheets y = 1.3308e-2 + 3.4813e-6x - 2.4528e-9x^2 + 3.2232e-13x^3 R^2 = 0.999 y = 4084.4 - 120.52x + 1.4112x^2 - 1.2627e-2x^3 R^2 = 1.000

SYSTEM AND METHOD FOR AIR TIME REMAINING CALCULATIONS IN A SELF-CONTAINED BREATHING APPARATUS

FIELD OF THE INVENTION

The present invention relates generally to self-contained breathing systems and more particularly to more effective calculations of remaining air time in systems with high tank pressures.

BACKGROUND OF THE INVENTION

Various forms of self-contained breathing apparatus form substantially the only means by which human beings are able to safely and effectively function in hostile atmospheric environments. In particular, a self-contained breathing apparatus are essential equipment for divers who wish to remain below the surface for periods of time exceeding their inherent lung capacity, whether for sport, pleasure or to further certain commercial operations such as salvaging, construction and the like. In addition, self-contained breathing apparatus forms essential equipment for service and rescue personnel such as firefighters, paramedics, and the like, that must operate in smoke-filled environments that often include highly toxic gases.

Needless to mention, such self-contained breathing apparatus must include a source of a breathable gas mixture which contains sufficient breathing gas for extended operations in hostile environments. Additionally, such systems must include an apparatus that facilitates delivery of the breathing gas to a user in a safe, effective manner. Pertinent to breathing gas delivery, is the desirability of being able to adequately determine the breathable gas content of a breathing apparatus (or respirator) and be able to express the gas content in terms of the amount of breathing time left available to a user (air time remaining or ATR).

Understanding just how much breathing gas remains in an apparatus and, therefore, how much breathing time this represents, is essential to people who must enter and work in hostile environments. A diver, for example, must understand how much air is remaining in the system in order to allocate sufficient time for a safe decompression program. Likewise, a firefighter must understand how much air time is remaining in order to provide sufficient time to effect a safe exit from a smoke-filled environment or one containing toxic or corrosive gases. Air time remaining is quite possibly the most critical metric with which a user of a self-contained breathing apparatus must be concerned.

Traditionally, self-contained breathing apparatuses can be viewed as falling into two general categories; open circuit and closed or semi-closed circuit. Open circuit systems are typically recognized by the common term SCUBA and represent the most commonly used form of breathing apparatus. Developed and popularized by Jacques Cousteau, open circuit scuba apparatus generally comprises a high pressure tank filled with compressed air, the tank coupled to a demand regulator which supplies the breathing gas to, for example, a diver at the diver's ambient pressure, thereby allowing the user to breath the gas with relative ease.

However, with open circuit scuba apparatus, even short duration dives at depths greater than 100 feet require a certain amount of decompression time which must be pre-calculated in order to ensure a sufficient volume of breathing gas remains after the dive in order to accommodate decompression. Accordingly, while relatively simple and inexpensive, open circuit scuba apparatus imposes stringent and non-linear constraints on dive time as a consequence of its construction and configuration. This has a direct impact on considerations of air time remaining.

The second form of self-contained breathing apparatus is the closed circuit or semi-closed circuit breathing apparatus, commonly termed a REBREATHER. As the name implies, a rebreather allows a user to "rebreathe" exhaled gas to thus make nearly total use of the oxygen content in its most efficient form. Since only a small portion of the oxygen a person inhales on each breath is actually used by the body, most of this oxygen is exhaled, along with virtually all of the inert gas content, such as nitrogen, and a small amount of carbon dioxide which is generated by the user. Rebreather systems make nearly total use of the oxygen content of the supply gas by removing the generated carbon dioxide and by replenishing the oxygen content of the system to make up for the amount that is consumed by the user.

In all of the above-mentioned cases, whether open circuit or closed or semi-closed circuit, breathing gas is provided in tanks of compressed air, or other gases, of well understood internal volumes, rated to contain breathing gas at particular maximum internal pressures. Indeed, compressed air tanks are often identified in terms of their internal volumetric content, i.e., 10 liter tank, 20 liter tank, and the like, or by an nominal breathing time which a tank would support when filled to its rated capacity, i.e., 30 minute tank, 60 minute tank, and the like.

The amount of breathing gas contained within a given tank can be calculated with reasonable accuracy by simply assuming the ideal gas law;

$$pV=MRT/m \tag{1}$$

where p is the internal gas pressure in the tank, V is the internal volume of the tank, M is the mass of the breathing gas contained within the tank, R is the universal gas constant (or molar gas constant), T is the temperature of the compressed gas in degrees K, and m is the molecular weight of the gas.

Given the ideal gas assumption above, air time remaining (ATR) can be calculated according to the formula;

$$(ATR) = \frac{p - p_{Reserve}}{-\frac{dp}{dt}} \tag{2}$$

where $p_{Reserve}$ is a chosen reserve pressure and $$\frac{dp}{dt}$$

is the instantaneous rate of change of pressure that is a measurement of how quickly gas is being consumed by a user. In practical terms, the instantaneous rate of change of change of pressure can be estimated by $\Delta p/\Delta t$ which is obtained by observing or measuring the change in tank pressure over a relatively short period of time, i.e., approximately 1 minute.

For internal tank pressures in the region of about 2000 psi and below, air time remaining predictions resulting from calculations conducted in accordance with Equations (1) and (2) above are normally sufficiently accurate to allow reasonably safe use. However, modern material science and fabrication techniques have resulted in self-contained breathing apparatus having compressed breathing gas tanks which contain breathing mixtures at pressures of about 4500 psi and even greater. High pressure tank systems such as these are becoming more and more commonplace in both professional and recreational respirator apparatus.

As is well understood by those having skill in the art, the linear ideal gas law, as represented in Equation (1) above, becomes increasingly inaccurate with increasing pressure. Not only does the linear ideal gas law become inaccurate with increasing pressure, but also these inaccuracies can be further perturbed by the molecular make-up of the breathing gas. Each particular gas mixture will have its own particular phase or state response as a function of pressure. Thus, pressure related non-linearities and the ideal gas law for a compressed air mixture will be different than pressure related non-linearities in the case of heliox, for example.

In addition to the deviation of a real gas from the ideal gas law, tank volumes are not always constant. In particular, fire fighters commonly use tanks that are manufactured of wrapped composite materials that, while characterized as generally rigid, still exhibit significant amounts of volumetric expansion at high internal pressures. This volumetric expansion contributes to further non-linearities in air time remaining (ATR) calculations. Finally, pressure transducers contribute an additional source of non-linearities that must be taken into account in ATR calculations.

However caused and to whatever extent exhibited, pressure related non-linearities can lead to considerable inaccuracies in air time remaining predictions when ATR predictions are calculated in accordance with Equations (1) and (2) above. Such inaccuracies in ATR predictions lead to significant safety problems, particularly when a diver's planned activity schedule and/or decompression profile is calculated on one basis when it actually conforms to another. Firefighters and rescue workers are unable to plan activity in a hostile environment with the strict efficiencies necessary for such high risk activities. Accordingly, there exists a need for self-contained breathing apparatus or respirator systems which operate in conjunction with high breathing gas tank pressures that are able to more effectively and accurately take pressure related non-linearities into account when making air time remaining (ATR) calculations. Such systems should be able to account for different non-linearities exhibited by different breathing gas mixtures.

SUMMARY OF THE INVENTION

In a self-contained breathing apparatus of the type including breathing gas contained under pressure in a breathing gas supply tank, a method for accurately determining air time remaining calculates ATR on the basis of a mass of breathing gas contained in the tank by determining a gas supply metric for gas contained in the tank and converting the gas supply metric into a mass. In determining the gas supply metric, the method involves measuring an internal pressure of the tank and solving a non-linear equation which expressly accounts for the non-linearity of a pressure:mass relationship at high pressures. The non-linear equation solution defines a set of ordered pairs of pressure:mass data which are stored in a look-up table.

In particular, the method includes the step of curve fitting a power function to the set of ordered pairs of pressure:mass data, with the function defining a corresponding rate of change of mass from a rate of change of pressure.

In another aspect of the invention, a system for effecting accurate air time remaining determinations in a self-contained breathing apparatus includes sensor means for determining an amount of pressure of a breathing gas within a gas supply tank. Processor means converts measured pressure into a mass equivalent of breathing gas in accordance with a non-linear equation. The processor means thereby determining the air time remaining in the gas supply tank on the basis of an equivalent mass of breathing gas contained in the tank, rather than the measured pressure. A memory is coupled to the processor means in which a set of ordered pairs of pressure:mass data are stored in a look-up table. The ordered pairs of pressure:mass data are produced by solving the non-linear equation, which expressly accounts for the non-linearity of a pressure:mass relationship at high pressures.

The processor means curve fits a power function to the set of ordered pairs of pressure:mass data whereby the function defines a corresponding mass value from a pressure value.

DESCRIPTION OF THE DRAWINGS

These and other features, aspects, and advantages of the present invention will be more fully understood when considered with respect to the following detailed description, appended claims, and accompanying drawings, wherein:

DETAILED DESCRIPTION OF THE INVENTION

Figure 1:
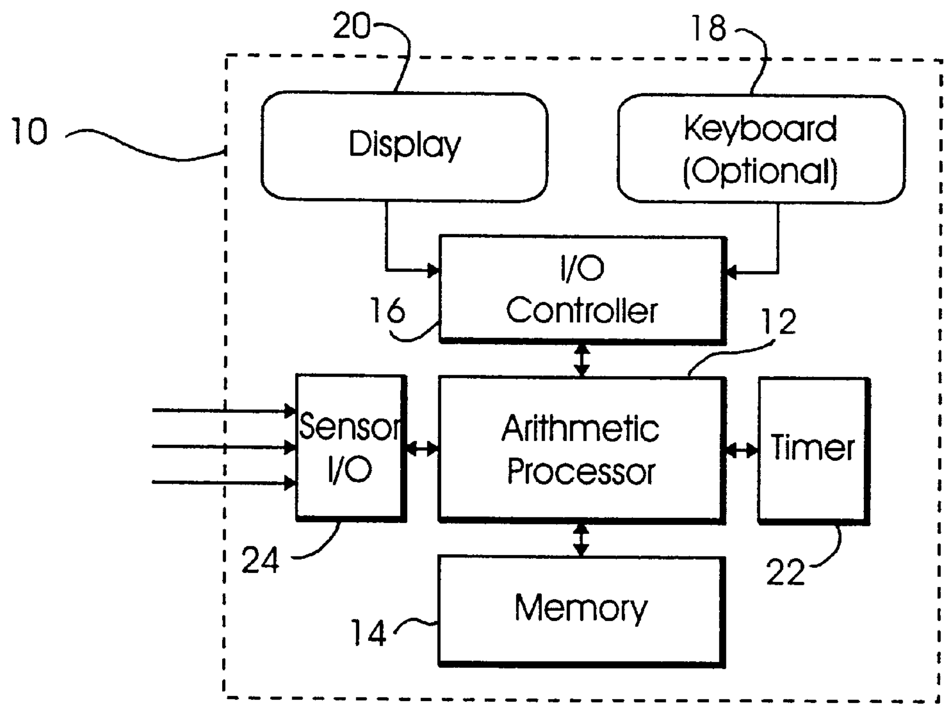
FIG. 1 is a semi-schematic generalized block level diagram of a microcontroller-based gas system metric calculator suitable for use in connection with the present invention.

The primary limitation of conventional air time remaining (ATR) calculation system lies in the fact that the equations forming the basis of the calculations are expressed in linear form and do not take into account the non-linear nature of the pressure/mass relationship at substantially high gas pressures, i.e., pressures greater than about 2000 psi. The present invention is directed to a system and method for effecting accurate air time remaining calculations for self-contained breathing apparatus that take high pressure related non-linearities into account. In particular, practice of principles of the present invention involves the recognition that what is being consumed (drawn from the tank) by a diver, firefighter or other user of a self-contained breathing apparatus, is a particular mass of breathing gas, not a quantity of pressure. Thus, air time remaining (ATR) calculations are performed with respect to mass M, as opposed to being performed with respect to pressure p as is done conventionally.

Three independent sources of non-linearity; real gas effects, tank volume changes, and non-linearities caused or introduced by various pressure transducers have all been identified as contributing potentially important errors in the proper estimation of air time remaining (ATR). Because each source of non-linearities is independent from the others, one approach to a deterministic calculation of ATR would be to quantify each source of non-linearity separately.

An equally effective approach, and one that is particularly advantageous, is to empirically evaluate the contribution of the combination as a whole. A particular methodology for performing this evaluation would be to measure a particular tank pressure as a function of time, as breathing gas is being removed from the tank at a constant rate. In this regard, constant gas removal may be performed with a conventional breathing machine, which is set to emulate a constant lung capacity taking a fixed number of breaths per time period (10 breaths per minute, for example).

In particular, a methodology for empirically quantifying the effects of various non-linearities in order to define an accurate estimate of air time remaining (ATR) begins by assuming an analytical form for the mass of breathing gas within a tank. Since ATR is calculated by dividing mass by the rate of change of mass, any constants associated with dimensionality, units, or the like can be ignored and the analytical form expressed as a mass equivalent MP. This analytical form is expressed as:

$$MP=[1+\alpha P+\beta P^2+\gamma P^3]P \qquad (3)$$

where MP is mass equivalent, P is pressure and where α, β and γ are constants. By measuring tank pressure as a function of time while gas is being depleted at a constant rate, the values of the constants α, β and γ may be established by differentiating mass equivalent with respect to time in the following manner:

$$\frac{dMP}{dt}=\frac{dP}{dt}[1+2\alpha P+3\beta P^2+4\gamma P^3] \qquad (4)$$

Since the time derivative of the mass equivalent $$\frac{dMP}{dt}$$

is, by definition a constant, one need simply plot $$\left[\frac{dP}{dt}\right]$$

as a function of pressure in order to determine the values of α, β and γ. The time derivative of mass equivalent is necessarily a constant because of the initial conditions of the empirical determination, i.e., gases being depleted at a constant rate with a breathing machine, requiring the mass equivalent rate of change to be a constant value.

Figure 6:
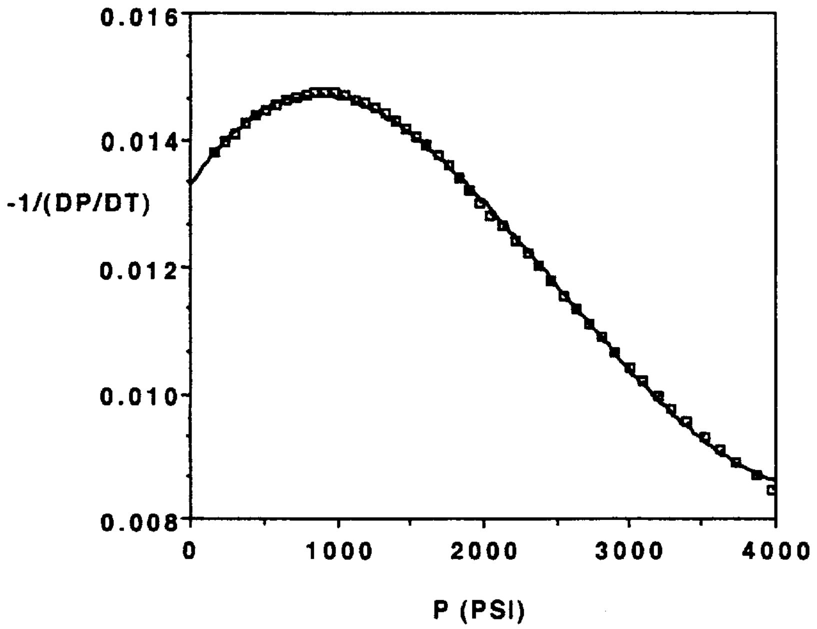
FIG. 6 is a plot of pressure verses time in order to develop a analytical equation fit to the data in accordance with the methodology of the invention.

Determining the values of α, β and γ involves fitting the pressure/time plot with a cubic function, as depicted in the illustration in FIG. 6, and then differentiating the resultant analytical fit.

In the illustration of FIG. 6, empirical data taken from a tank in accordance with the invention, has pressure plotted as a function of time and the analytical fit for the data points can be seen to be a cubic expression, i.e., $y=4084.4-120.52x+1.4112x^2-1.2627e^{-2}x^3$. When appropriate values for pressure are substituted for y, and appropriate values of time (in minutes) are substituted for x, and the resultant analytical fit differentiated with respect to time, a value for $$\left[\frac{dP}{dt}\right],$$

can be determined as follows:

$$\frac{dP}{dt}=-120.52+2\times1.4112\times t-3\times1.2627\times10^{-2}t^2 \qquad (5)$$

Figure 7:
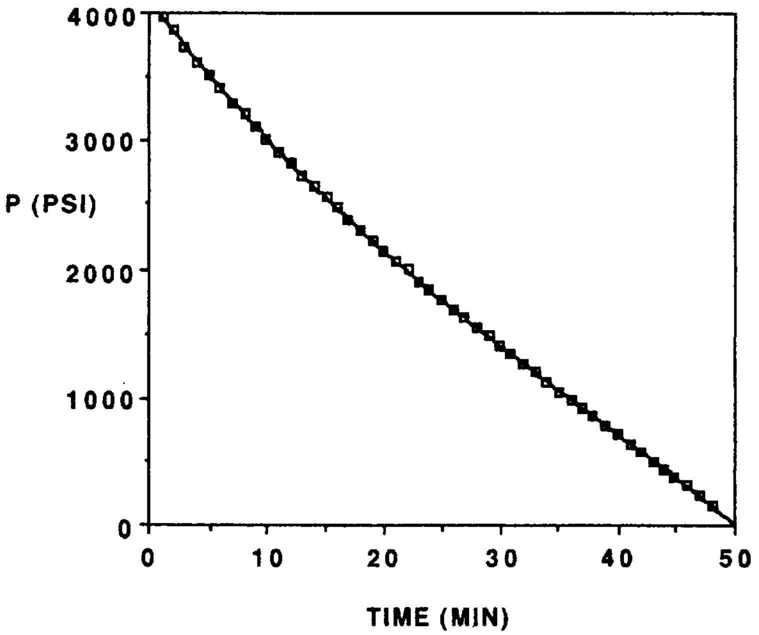
FIG. 7 is a plot of a pressure derivative verses pressure in accordance with the methodology of the invention.

Once the rate of change of pressure with respect to time is determined, it remains to only plot $$\left[\frac{dP}{dt}\right]^{-1}$$

as a function of pressure in order to obtain numerical values for the rate of change of mass equivalent (MP) with respect to time, as well as the values of the constants α, β and γ. A plot of $$\left[\frac{dP}{dt}\right]^{-1}$$

versus pressure is illustrated in FIG. 7.

Using empirical data acquired during practice of the methodology described above, particular numerical values for the time rate of change of equivalent mass and the constants α, β and γ were calculated to be as follows:

$$-\frac{dMP}{dt}=\frac{100}{1.3308}=75.14 \qquad (6)$$

$$\alpha=\frac{3.4813\times10^{-6}}{2\times1.3308\times10^{-2}}=1.308\times10^{-4} \qquad (7)$$

$$\beta=\frac{-2.4528\times10^{-9}}{3\times1.3308\times10^{-2}}=-6.144\times10^{-8} \qquad (8)$$

$$\gamma=\frac{3.2232\times10^{-13}}{4\times1.3308\times10^{-2}}=6.055\times10^{-12} \qquad (9)$$

In order to calculate air time remaining (ATR), it is important to recognize that a particular pressure reserve value must be introduced into the expression in order to avoid erroneous results that necessarily obtain when the reserved pressure value falls below a characteristic first stage regulator pressure. In common implementations, first stage regulator pressure is typically about 150 psi. Accordingly, a tank reserve pressure of about 300 psi is chosen in order to minimize error that is introduced as a regulator begins to fail. Air time remaining (ATR), to a tank pressure reserve of 300 psi, is calculated in accordance with the following:

$$ATR=\frac{(MP-300)}{-\frac{dMP}{dt}}=\frac{(MP-300)}{75.14} \qquad (10)$$

In practical terms, if mass equivalent MP is incrementally adjusted, and pressures p calculated for the resultant mass equivalent, a range of pressure:mass equivalent (p:MP) data pairs may be produced which express the pressure-MP relationship over a range of specified mass equivalents.

Once the p:MP data pairs are developed, one is able to apply curve fitting techniques to these data points in order to develop an expression (i.e., to calculate) mass MP as a function of pressure p directly. Alternatively, the p:MP data points are used to construct a table of related pressure:MP values. For any given measured pressure p, a corresponding mass equivalent MP can be determined by simply consulting the table to obtain mass directly, or interpolating between two values of mass if the input pressure p does not coincide precisely with the table value.

Irrespective of how the pressure:MP data points are acquired or expressed, air time remaining (ATR) is predicted in accordance with the present invention by first calculating or determining a mass equivalent value MP from a measured pressure p, using the methodology of the present invention, and then second, to calculate air time remaining as a function of mass equivalent MP and the rate of change of mass as expressed by the ATR relation determined in Eq. 10, above:

$$ATR = \frac{MP - P_{Reserve}}{-\frac{dMP}{dt}} \tag{11}$$

In this particular instance, $p_{Reserve}$ refers to a chosen value of reserve pressure depending on the characteristics of the chosen tank. It will be useful to use the above-described pressure:MP relationship to develop a suitable value for the chosen reserve pressure, if additional accuracy is desired. One need only identify a particular chosen reserve pressure and then proceed in accordance with practice of the invention. As was the case with calculating the instantaneous rate of change of pressure, calculations with respect to the instantaneous rate of change of mass equivalent, i.e., dMP/dt, might be made by estimation. The ΔMP/Δt approximation might be suitably obtained by observing a change in mass equivalent over a specified period of time, i.e., 1 minute for example, in cases where rigorous accuracy is not required.

It should be understood that gas consumption and thus, other rate of change of mass in the system, is a dynamic quantity and depends greatly on various external conditions. Such external conditions might include a diver's depth in the case of an open system scuba apparatus, whether or not a user is exerting themselves, and the like. This change in the rate of change of mass is, in itself, not problematic, since mass rate of change can be continuously calculated and continuously updated in order to provide smooth, realistic and timely air time remaining calculations.

The methodology of the present invention, i.e., calculating air time remaining using a non-linear equation to first predict mass content from measured pressure and then use these calculated data and their rate of change in order to predict air time remaining, has been verified by experimentation and practical application. An example of the differences between air time remaining calculations performed using the linear ideal gas law as the equation of state and the non-linear empirically derived expressions are depicted in the following Table 1 for ordinary air under pressure in a breathing gas supply tank having a 4-liter capacity.

TABLE 1

| TIME (MIN) | PRESS (PSIA) | MASS EMP | ATR LIN | ATR EMP | DIFF |
|---|---|---|---|---|---|
| 01 | 3971 | 3691.9 | 31.2 | 45.1 | 14.0 |
| 05 | 3509 | 3382.9 | 29.9 | 41.0 | 11.1 |
| 10 | 3008 | 3015.0 | 28.2 | 36.1 | 7.9 |
| 15 | 2553 | 2640.4 | 26.0 | 31.1 | 5.2 |

TABLE 1-continued

| TIME (MIN) | PRESS (PSIA) | MASS EMP | ATR LIN | ATR EMP | DIFF |
|---|---|---|---|---|---|
| 20 | 2140 | 2263.9 | 23.2 | 26.1 | 2.9 |
| 25 | 1762 | 1890.4 | 19.9 | 21.2 | 1.3 |
| 30 | 1401 | 1512.1 | 15.7 | 16.1 | 0.4 |
| 35 | 1052 | 1132.6 | 11.0 | 11.1 | 0.0 |
| 40 | 708 | 753.3 | 6.0 | 6.0 | 0.1 |
| 45 | 368 | 382.8 | 1.0 | 1.1 | 0.1 |
| 46 | 299 | 309.1 | 0.0 | 0.1 | 0.1 |

In the foregoing Table 1, the term MASS EMP refers to the mass which is calculated from the corresponding pressure expressed in psia from a curve fit derived from the previously described empirical procedure. As can be seen from Table 1, the air time remaining predictions using raw pressure and a linear state equation, and expressed under the heading "ATR LIN", are substantially different than the air time remaining predictions made using the system mass calculated from the pressure, expressed under the heading "ATR EMP", particularly in the high pressure portion of the regime. As can be seen, air time remaining calculations based upon mass are accurate to within less than 1 minute, whereas air time remaining calculations based on raw pressure are over 14 minutes in error at a gas pressure of about 4000 psi.

Air time remaining calculations of the sort described above are suitably performed in the context of a complete self-contained breathing apparatus including a source of compressed breathing gas, such as a tank, some means of transferring compressed breathing gas from the tank to a user, such as a regulator, and an electronic gas metric calculation device coupled into the system in a manner which facilitates air time remaining calculations as described above. An exemplary embodiment of such a breathing gas metric calculation device is depicted in semi-schematic block diagram form in FIG. 1. The gas metric calculator 10 might be similar in construction and design to a dive computer of the type commonly used in connection with open circuit scuba diving apparatus. Although the exemplary embodiment of FIG. 1 is described in connection with a dive computer, it should be understood that a gas metric calculation device of similar construction and application may be used in connection with respirator systems, whether open, closed or semi-closed circuit, used by firefighters and other rescue personnel. All that is required is that the gas metric calculation device be capable of performing accurate air time remaining calculations in accordance with the invention, as described above.

The gas metric calculation device 10 is suitably configured as a computerized device and includes an arithmetic processor 12 such as a microcontroller, microprocessor, or any other form of general purpose or purpose-built integrated circuit computational engine. The processor 12 might include internal memory or, alternatively, be coupled to a memory device 14 which functions to hold the system's operational instructions, various look-up tables, data pairs, and the like. The memory 14 might be either dynamic or static and might include ROM, PROM, EPROM, as well as SRAM or DRAM components.

The calculation device 10 also includes an input/output (I/O) controller 16 which functions as an interface between the processor 12 and (optionally) an input device such as a keypad or touchpad 18. The I/O controller 16 further functions to drive a display screen 20 which displays information calculated by the processor 12 in response to either user inputs to the keypad or touchpad device 18, or alternatively in response to program steps operating on input parameters incorporated in the microprocessor. It should be recognized that the I/O controller 16 may be provided as a separate integrated circuit component or, alternatively, may be provided as a functional block to the processor 12, at the discretion of the system designer. Likewise, a timer 22 might be provided as an off-chip component to the processor 12 or alternatively, might be included as a component portion of the processor circuitry. The timer 22 provides not only timing signals to the processor 12, but also provides timing synchronization signals which allow accurate time calculations necessary for calculating rates of change and, thence, air time remaining. The metric calculator 10 further includes sensor I/O ports 24 which interface the processor 12 with a variety of off-chip sensors, such as a tank pressure sensor, depth sensor, mass flow controller, oxygen sensor, and the like. Coupling the sensors to the processor 12 allows the processor to receive necessary information from the sensors in order to perform the requisite air time remaining calculations in accordance with the invention.

Figure 4:
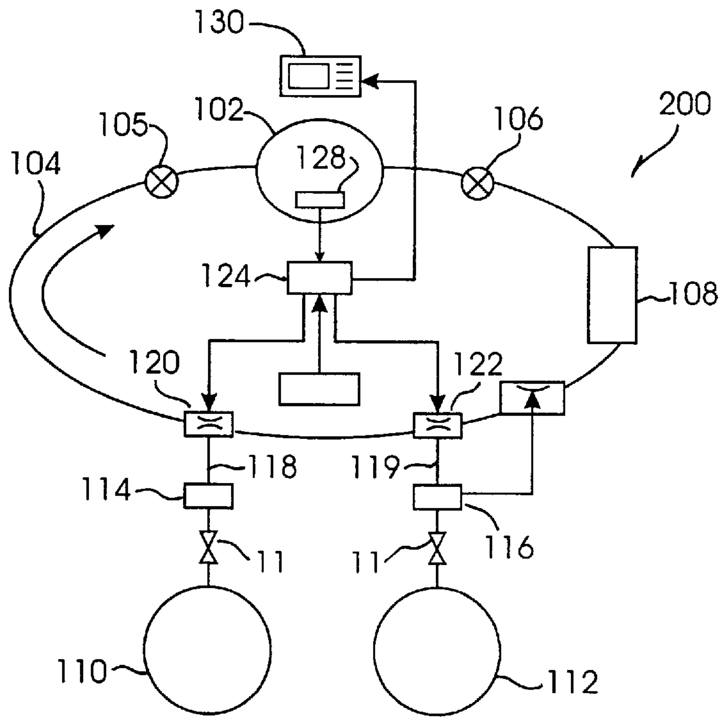
FIG. 4 is a semi-schematic generalized block level diagram of a semi-closed circuit rebreather system including a breathing gas supply tank, gas system metric sensors and a gas system metric calculator as in FIG. 1.
Figure 5:
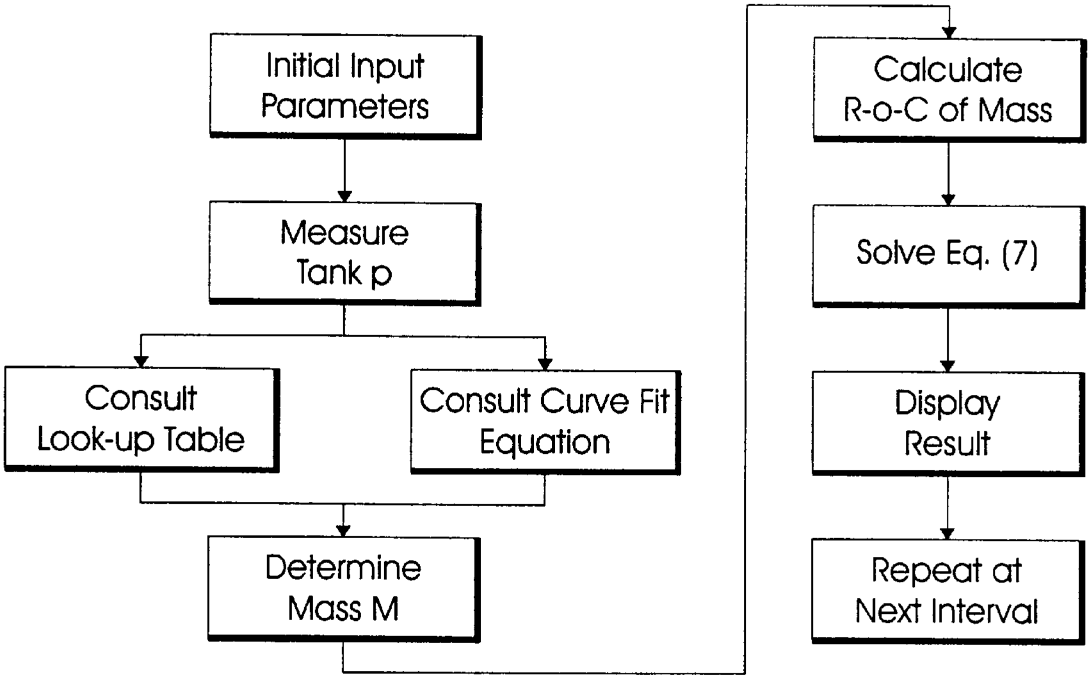
FIG. 5 is a simplified flow diagram detailing the operational steps of calculations in accordance with the invention.

For example, and with regard to the flow diagram of FIG. 4, a user might enter certain initial input parameters to the device 10 by making appropriate entries on the keypad or touchpad 18 in one configuration, or input parameters might be taken from memory. Initial input parameters would include certain initialization data such as tank volume V, the desired reserve mass $M_{Reserve}$ or alternatively, desired reserve pressure $P_{Reserve}$ and the gas type (air, oxygen, heliox, nitrox, etc.) so as to define the appropriate coefficient set used by the non-linear equation to effect appropriate calculations. Once the initial input parameters are entered, a suitable look-up table containing the appropriate pressure:mass data pairs and contained in memory 14, is identified for use by the processor 12 in making air time remaining calculations for the specific breathing gas mixture being used. Alternatively, a particular one of a multiplicity of curve fit equations, each generated in accordance with the invention and each specific to a particular breathing gas mixture, might be selected for use by the processor 12 in making air time remaining calculations for the selected breathing gas mixture.

During use, a tank pressure indicator or sensor measures the pressure of the breathing gas inside the tank and provides the pressure value to the processor 12 through sensor interface 24. Once the processor 12 receives the measured pressure, it either consults the appropriate look-up table previously identified or consults the appropriate curve fit equation in order to determine the corresponding equivalent mass of breathing gas associated with that particular measured tank pressure. That particular value of mass is subtracted from a previous value of mass calculated during a previous well defined timing interval (approximately 1 minute) in order to define a time-rate-of-change of mass $\Delta M/\Delta t$. The system next uses the determined mass, previously entered reserve mass and rate-of-change of mass values in a solution of the air time remaining calculation expressed in Equation 11. The result is displayed on the display screen 20.

Air time remaining calculations are suitably performed at every pre-set interval, such as 1 minute, and may be simply stored in memory 14 until accessed by the user or alternatively, might be continually updated in a portion of the display screen 20. However made available to the user, it is sufficient that a system calculate air time remaining in accordance with the invention on a periodic basis such that air time remaining calculation results are always timely available to the user. As an additional feature, the system 10 might also have the capability of alerting a user when the air time remaining calculation gives a value that approaches or reaches a particular pre-set threshold, indicating that the remaining mass of breathing gas is approaching or has reached the reserve $P_{Reserve}$ value. This feature is particularly important when the system 10 is used in connection with an underwater breathing apparatus such that a diver may have sufficient air time remaining to complete a decompression program. In this regard, it should be noted that the initial input parameters need not be entered using the keypad 18, but might be calculated from various external data. For example, a reserve mass or pressure might be calculated by the processor 12 to conform with a pre-determined and pre-entered dive profile. The reserve mass or pressure calculations might be done in a manner that conforms with depth dependent gas flow control algorithms such as described in U.S. Pat. No. 5,924,418, the entire contents of which are expressly incorporated herein by reference.

Figure 2:
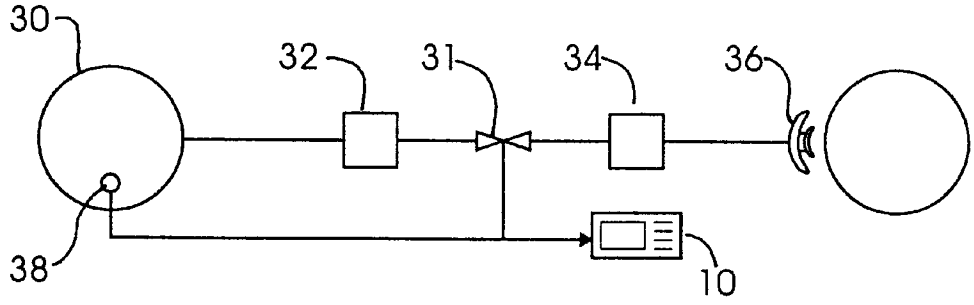
FIG. 2 is a semi-schematic generalized block level diagram of an open circuit breathing apparatus including a breathing gas supply tank, gas system metric sensors and the gas system metric calculation of FIG. 1.

A particular embodiment of an open circuit scuba apparatus, capable of operation in accordance with principles of the invention described above, is depicted in FIG. 2. The embodiment of FIG. 2 is illustrated as an open circuit demand-type system which utilizes compressed air tanks in combination with demand regulator valves which provide air from the tanks on demand from a user by the inhalation of air. A compressed air supply tank 30 is coupled to a first stage (high pressure) regulator 32 which conventionally includes an on-off valve 31 which reduces the pressure of air within the tank to a generally uniform low pressure value suitable for use by the rest of the system. Low pressure air (approximately 150 psi)is delivered to a second stage regulator 34 through a demand valve 36 in conventional fashion. Compressed air, at the cylinder pressure, is reduced to the user's ambient pressure in two stages, with the first stage reducing the pressure below the tank pressure, but above the ambient pressure, and the second stage reducing the gas pressure to the surrounding ambient pressure. The demand valve is typically a diaphragm actuated, lever operated spring-loaded poppet which functions as a one-way valve, opening in the direction of air flow, upon movement of the diaphragm by a user's inhalation of a breath.

The open circuit system of FIG. 2 further includes an electronic metric calculation device 10 such as was described above in connection with FIG. 1. The calculator 10 might be disposed anywhere about the person of the user and is mechanically coupled through a pressure line to the first stage regulator 32 in order to determine tank pressure. The calculator 10 might also be connected to a temperature sensor 40 that might be disposed within the breathing gas supply tank 10 and which might be used to effect more accurate calculations of air time remaining by providing a more accurate indication of temperature T.

A particular embodiment of a rebreather system, particularly a closed circuit rebreather system, capable of operation in accordance with principles of the invention described above, is depicted in FIG. 3. The components of the rebreather system of FIG. 3 suitably include a flow loop, generally indicated at 100, in turn comprising a flexible volumetrically defined counterlung 102 from which a user inhales and to which a user exhales a breathing gas mixture through a suitable mouthpiece. Counterlung 102 is coupled into the flow loop 100 by means of suitable low pressure hoses 104 which define the gas flow pass of the flow loop. Gas flow direction through the low pressure hoses 104 are controlled by first and second one-way check valves 105 and 106 which are disposed along the low pressure hoses 104 and positioned so as to define the flow of the breathing gas into and out of the counterlung 102. Carbon dioxide ($CO_2$)is removed from the exhaled gas volume by a $CO_2$ scrubber canister 108 which is disposed in the gas flow in a direction defined as down-stream from the counterlung 102. Breathing gas is supplied to the flow loop 100 by a breathing gas source suitably comprising first and second cylinders, 110 and 112, respectively, capable of receiving and holding a volume of a compressed breathing gas.

The tanks 110 and 112, respectively, are coupled to the flow loop 100 through on-off valves and respective high pressure regulators 114 and 116, respectively. The pressure regulators 114 and 116 regulate and reduce the gas flows from the tanks to a lower operating pressure suitable for low pressure hoses 104 comprising the rebreather flow loop 100. Low pressure regulated gas is coupled to the flow loop 100 by means of low pressure hoses 118 and 119, each of which are connected to introduce gas from their source tanks to individual mass flow control valves 120 and 122. During normal operation of the rebreather, mass flow control valves 120 and 122 determine the amount of gas from their respective tanks which is introduced to the system in order to maintain the partial pressure of the breathing gas within the specified range.

A signal processing circuit 124 is connected into the system so as to receive tank pressure information from tank pressure indicators 129 coupled to each supply tank and from an oxygen sensor 128 provided within the counterlung 102. The oxygen sensor 128 and pressure indicator 129 are electronically coupled to the signal processing circuit 124 and provide the signal processing circuit with information relating to the partial pressure of oxygen comprising the gas within the counterlung and a figure of merit corresponding to the remaining capacity of the supply tanks. It is, of course, axiomatic that the signal processing circuit 124 be one of a type capable of performing the calculations in accordance with the algorithm of the present invention, so as to develop timely and accurate air time remaining calculations. Accordingly, the signal processing circuit 124 is of the type described in connection with FIG. 1 and might comprise a dive computer or be provided separate from the computer and configured to electronically provide its computational results to such computer. In this regard, the signal processing circuit 124 is coupled to a data display device 130 such that its calculations may be visually available to a user.

Figure 3:
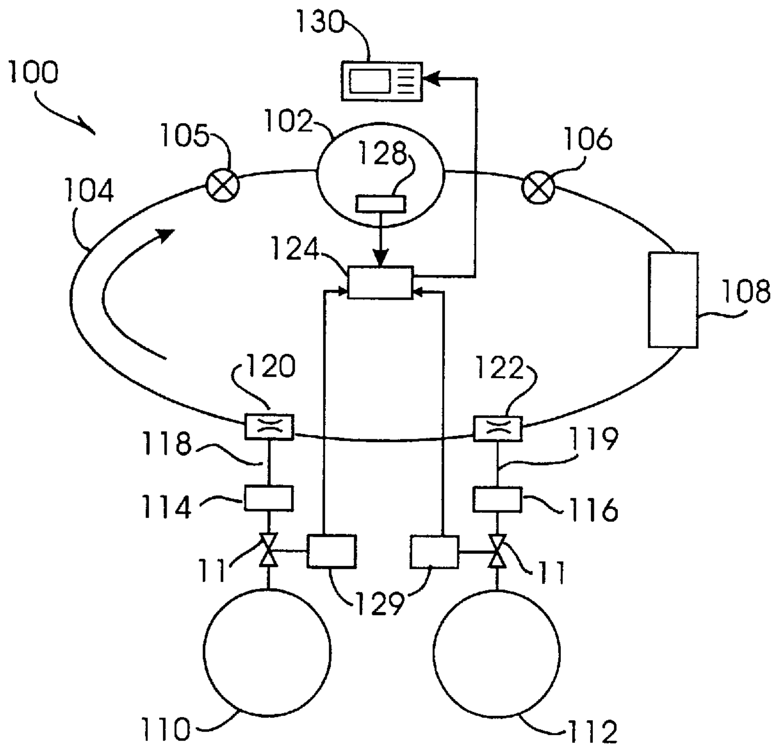
FIG. 3 is a semi-schematic generalized block level diagram of a closed circuit rebreather system including a breathing gas supply tank, gas system metric sensors and a gas system metric calculator as in FIG. 1.

FIG. 4 is a semi-schematic, generalized block level diagram of a semi-closed circuit rebreather system 200 which includes a breathing gas supply tank or tanks 110, 112, gas system metric sensors 120, 122 and 128 and a gas metric calculator 124 (a signal processing circuit) as described in connection with the embodiment of FIG. 3. The semi-closed circuit rebreather system of FIG. 4 differs from the closed circuit system of FIG. 3, only in its implementation of how a proper mixture of breathing gas is delivered to a counterlung for use by a diver. The components of semi-closed circuit rebreather systems are well understood in the art and need no further amplification, here. However, the ATR determination methodology according to the invention is particularly suited for inclusion in the capability of such systems. All that is required is a sensor which is able to determine tank pressure, and a signal processing circuit capable of performing the novel ATR determination analysis.

Reliable self-contained breathing apparatus have been disclosed which operate in accordance with an algorithm to accurately predict air time remaining so as to give a more particular indication to a user of the amount of time available on a particular apparatus, without causing any undue safety concerns. The embodiments described above have used particular non-linear analytical expressions as the primary determinant of the pressure:mass relationship at high pressures. As will be evident to those having skill in the art, any number of non-linear analytical expressions may be used, so long as they take into account the non-linear relationship between pressure and mass at tank pressures in excess of 2000 psi.

It will be recognized by those skilled in the art that various modifications may be made to the various illustrated and other embodiments of the invention described above, without departing from the broad inventive scope thereof. It will be understood therefore that the invention is not limited to the particular embodiments, arrangements or steps disclosed, but is rather intended to cover any changes, adaptations or modifications which are within the scope and spirit of the invention as defined by the appended claims.

What is claimed is:

1. A method for accurately determining air time remaining in a self-contained breathing apparatus of the type including breathing gas contained under pressure in a breathing gas supply tank, the method comprising:

determining a compensated gas supply metric for gas contained in the tank, the compensated gas supply metric being compensated for at least one non-linearity;

converting said compensated gas supply metric into a mass; and calculating air time remaining on the basis of a mass of breathing gas contained in the tank.

2. The method according to claim 1, wherein determining the compensated gas supply metric further comprises measuring an internal pressure of the tank, said internal pressure representing an amount of gas contained within the tank.

3. The method according to claim 2, wherein converting the compensated gas supply metric further comprises solving a non-linear equation expressly accounting for non-linearity of a pressure:mass relationship at high pressures, the equation solutions defining a set of ordered pairs of pressure:mass data.

4. The method according to claim 3, further comprising storing the set of ordered pairs of pressure:mass data in a look-up table.

5. The method according to claim 3, further comprising curve fitting a function to the set of ordered pairs of pressure:mass data, the function defining a corresponding mass value from a pressure value.

6. The method according to claim 3, the non-linear equation including a set of coefficients, the set of coefficients being separately defined for each of a multiplicity of breathing gas mixtures.

7. In a self-contained breathing apparatus of the type including breathing gas contained under pressure in a breathing gas supply tank, a system for effecting accurate air time remaining determinations, comprising:

sensor means for determining a pressure of a breathing gas within the supply tank;

processor means for converting a pressure into a mass of breathing gas in accordance with a non-linear equation; and processor means for determining air time remaining on the basis of a mass of breathing gas contained in the tank.

8. The system according to claim 7, further comprising a memory coupled to the processor means, the memory holding a set of ordered pairs of pressure:mass data, configured as a look-up table.

9. The system according to claim 8, wherein the set of ordered pairs of pressure:mass data are produced by solving a non-linear equation expressly accounting for non-linearity of a pressure:mass relationship at high pressures.

10. The method according to claim 9, wherein a function is curve fitted to the set of ordered pairs of pressure:mass data, the function defining a corresponding mass value from a pressure value.

11. The system according to claim 9, the non-linear equation including a set of coefficients, the set of coefficients being separately defined for each of a multiplicity of breathing gas mixtures.

* * * * *